United States Patent
Majeed et al.

(10) Patent No.: US 6,998,502 B1
(45) Date of Patent: Feb. 14, 2006

(54) CONVENIENT PROCESS OF MANUFACTURE FOR DIFLUOROMETHYLORNITHINE AND RELATED COMPOUNDS

(75) Inventors: Muhammed Majeed, Piscataway, NJ (US); Kalyanam Nagabhushanam, North Brunswick, NJ (US); Keshava Rao Rapole, Edison, NJ (US); Ravikrishna Chebolu, Plainsboro, NJ (US)

(73) Assignee: Sabinsa Corporation, Piscataway, NJ (US)

( * ) Notice: Subject to any disclaimer, the term of this patent is extended or adjusted under 35 U.S.C. 154(b) by 0 days.

(21) Appl. No.: 10/236,992

(22) Filed: Sep. 5, 2002

(51) Int. Cl.
*C07C 205/00* (2006.01)

(52) U.S. Cl. .................................................. 560/25

(58) Field of Classification Search ................. 560/125
See application file for complete search history.

(56) References Cited

U.S. PATENT DOCUMENTS 4,330,559 A * 5/1982 Bey et al. ................... 514/564

* cited by examiner

*Primary Examiner*—Taofio Solola
*Assistant Examiner*—Robert Shiao
(74) *Attorney, Agent, or Firm*—Law Offices of Mitchell P. Novick; Benjamin Appelbaum, Esq.

(57) ABSTRACT

A process for the manufacture of α-Difluoromethylornithine, analogs and derivatives is described from ornithine hydrochloride or from $N^\delta$-phthaloyl ornithine hydrochloride, conversion to an alkyl ester, conversion to solid derivatives through the formation of Schiff bases, subsequent halomethylation using suitable bases and hydrolysis.

1 Claim, No Drawings

CONVENIENT PROCESS OF MANUFACTURE FOR DIFLUOROMETHYLORNITHINE AND RELATED COMPOUNDS

BACKGROUND OF THE INVENTION

α-Difluoromethylornithine (DFMO) is an amino acid associated with diverse biological functions and utility. It is a suicide enzyme inhibitor of pyridoxal phosphate-dependent ornithine decarboxylase. This amino acid has been found to possess curative properties against parasitic diseases like African sleeping sickness, benign prostate hypertrophy (U.S. Pat. No. 4,330,559), anti tumor (BE 881209), facial hair removal (U.S. Pat. No. 4,720,489; U.S. Pat. No. 4,648,394) etc. The present invention describes an industrially applicable process of manufacture of the amino acid DFMO and other structurally related compounds.

RELATED PRIOR ART

U.S. Pat. No. 4,330,559 describes a process of manufacture wherein ornithine hydrochloride is converted to a Schiff base intermediate with benzaldehyde. This Schiff base intermediate is an oil and unstable as other workers in this field (see Seki et al) had found out and commented. The alkylation process described within the patent involves the use of lithiumdiisopropyl amide whose generation requires a strong base such as butyl lithium, a pyrophoric chemical. Such bases are hazardous to use at industrial scale.

Seki et al describe a method of preparation of DFMO from ornithine dihydrochloride. They refer to the drawbacks in U.S. Pat. No. 4,330,559, especially to the instability of the Schiff base used in U.S. Pat. No. 4,330,559 which could not be purified by either distillation or chromatography. Seki et al used the chemistry of isocyanate groups in their synthesis. However many of their intermediates are not crystalline solids but oils and they require purification by column chromatography. Such methods of purification are very inconvenient at industrial levels.

Swiss patent CH 672 124 starts with malonic acid diethyl ester and in a sequence of chemical transformations describes the synthesis of DFMO. The number of steps involved is too many and include a hydrogenation step using Raney Nickel in the process.

Russian workers (Osipov et al) have described a process of synthesis of α-DFMO which utilizes highly specialized and not easily accessed chemicals as starting materials. The process also incorporates a hydrogenation step.

REFERENCES CITED

BE 881209 (1980).
Bey, P.; Vevert, J-P.; Dorsselaer, V. V.; Kolb, M. (1979) Direct synthesis of α-halogenomethyl-α-amino acids from the parent α-amino acids, *J Org Chem.*, 44: 2732–2742.
Jpn. Kokai Tokkyo Koho, 2001181247, 03 Jul. 2001.
Metcalf, B. W.; Bey, P.: Danzin, C; Jung, M. J.; Casara, P.; Vevert, J. P.(1978) Catalytic irreversible inhibition of Mammalian Decarboxylase (E.C. 4.1.1.17) by substrate and product analogues *J Am Chem Soc.*, 100: 2551–53.
Osipov, S. N.; Golubev, A. S.; Sewald, N.; Burger, K. (1997) New efficient synthesis of α-Difluoromethyl- and α-trifluoromethyl-Ornithine, *Tetrahedron Lett.*, 38: 5965–5966.
Osipov, S. N.; Golubev, A. S.; Sewald, N.; Michel, T.; Kolomiets, A. F.; Fokin, A. V.; Burger, K. (1996) *J Org Chem.*, 61: 7521–7528.
Seki, M.; Suzuki, M.; Matsumoto, K. (1993) Convenient synthesis of α-Difluoromethylornithine, *Biosci. Biotech. Biochem.*, 57: 1024–1025.
Swiss Patent, (1989) CH 672 124.
U.S. Pat. No. (1982) 4,330,559.
U.S. Pat. No. (1988) 4,720,489.
U.S. Pat. No. (1997) 4,648,394.

Present Invention

The invention sought to be patented involves the synthesis of compounds represented below

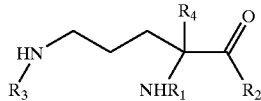

wherein in I

R$_1$ is hydrogen;
R$_2$ is hydroxy, C$_1$–C$_8$ alkoxy, —NR'R", wherein R'and R" are independently hydrogen, C$_1$–C$_8$ alkyl group;
R$_3$ is hydrogen;
R$_4$ is —CH$_2$F, —CHF$_2$, —CF$_3$,
and the salts thereof I through the base catalyzed halomethylation of the intermediates of orthogonal protected II and subsequent hydrolysis of the resultant products. The structure of II is represented by

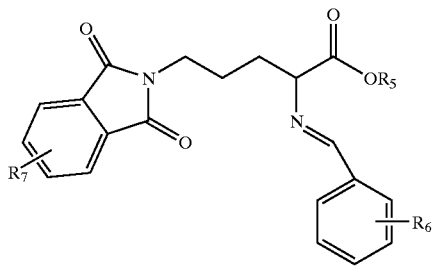

wherein in II,

R$_5$ is hydrogen, C1–C8 alkyl group;
R$_6$ is a halogen on the phenyl group such as o,m,p-chloro or o,m,p-bromo; or dihalogen substituents such as 3,4-dichloro; 2,6-dichloro; 3,4-dibromo and other positional isomers thereof; or polyalkoxy substituents; and
R$_7$ is hydrogen, C$_1$–C$_4$ alkyl, halogen substituents such as chlorine, bromine.

The products of the said halomethylation on II yield the products IIa which need not be isolated and could be hydrolyzed in situ to give the appropriate I directly or subsequently transformed to an appropriately substituted I by simple, known methods of synthesis.

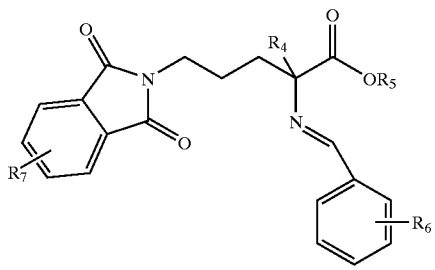

IIa

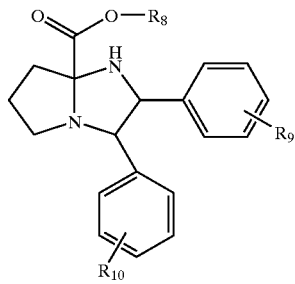

IV wherein
$R_9$ and $R_{10}$ are o-nitro and/or p-nitro substituents.

A similar behavior of cyclization was observed for compounds such as

The target materials represented by I are also derived through the base catalyzed halomethylation of the intermediates represented by III and subsequent hydrolysis of the resultant products to I or can be subsequently transformed to an appropriately substituted I by simple, known methods of synthesis.

The structure of III is represented by

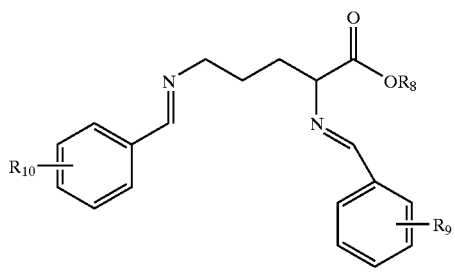

III

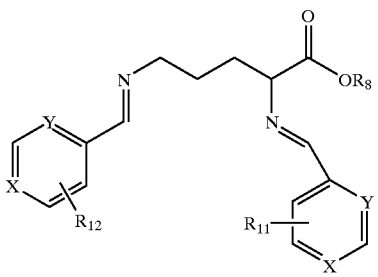

Va X = N, Y = CH
Vb X = CH, Y = N
Vc X = N, Y = N wherein in III
$R_8$ is hydrogen, $C_1$–$C_8$ alkyl;
$R_9$ is a halogen such as 4-chloro; 4-bromo; or dihalogen substituents such as 3,4-dichloro; 2,6-dichloro; 3,4-dibromo; poly alkoxy; 3-nitro; and
$R_{10}$ is a halogen such as 4-chloro; 4-bromo; or dihalogen substituent such as 3,4-dichloro; 2,6-dichloro; 3,4-dibromo; poly alkoxy; 3-nitro.

The products of the said halomethylation of III will give rise to IIIa which need not be isolated but can be hydrolyzed to I as described further in the Examples below.

wherein $R_8$ is as specified earlier.
$R_{11}$ and $R_{12}$ are independently alkyl, hydroxyalkyl, —OH functionality to give corresponding VI

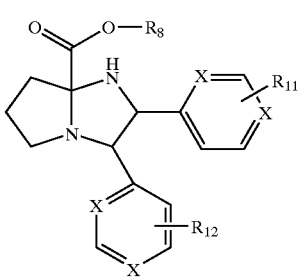

VI a X = N, Y = CH
VI b X = CH, Y = N
VI c X = N, Y = N wherein $R_8$, $R_{11}$, $R_{12}$ are as specified earlier.

The bases used for the base catalyzed halomethylation of II and III could be chosen from the group consisting of lithiumhexamethyldisilazide, sodiumhexamethyldisilazide and potassium hexamethyl disilazide; more specifically lithiumhexamethyldisilazide in solvents such as tetrahydrofuran, dioxan, hexane, aromatic solvents such as toluene, more specifically the solvent tetrahydrofuran. In the examples cited, hexamethyldisilazide is used in a solution of tetrahydrofuran. The stability of this base allows the solvent tetrahydrofuran to be removed and replaced with another desired solvent. The bases could also be chosen from sodium hydride or potassium hydride, with the solvents of reaction being tetrahydrofuran or dimethylformamide as the embodiments in the ensuing Examples will illustrate.

IIIa

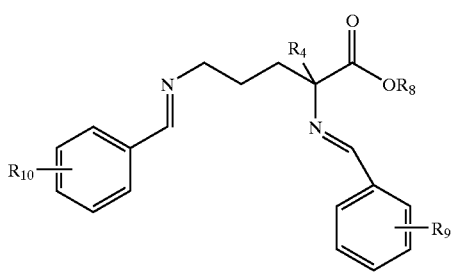

Certain intermediates III, wherein $R_9$ and $R_{10}$ are o-nitro and/or p-nitro, were not suitable as they rearrange concomitantly in the reaction medium to bicyclic compounds such as The intermediates I and II that are embodied and illustrated in this invention are convenient, crystalline solids and lend themselves to easy purifications by simple crystallization. The intermediate I and II are stable on storage under ordinary conditions; they can be dried very easily and satisfactorily for their ultimate intended use in the moisture-sensitive base catalyzed reaction of halomethylation. Thus, these stable intermediates facilitate the industrial production of DFMO by eliminating the need to synthesis them during each DFMO production run.

The temperature of the halomethylation can be chosen between −40° C. to +80° C. more advantageously between 0° C. to 40° C.

The process involves the addition of base such as lithiumhexamethyldisilazide to a solution of II or III followed by passing of the appropriate halogenated methane gas through the reaction mixture to give rise to IIa or IIIa; The process works equally well when the said base in an appropriate solvent is added to the solid form of II or III as one embodiment of this invention.

The present invention also describes inter alia a convenient method of esterification of amino acid ornithine or its salts as exemplified by Example I in contrast to earlier methods in prior art involved cumbersome or more corrosive reagents as passage of gaseous hydrogen chloride (U.S. Pat. No. 4,330,559) or thionyl chloride (Japan Kokai 2001181247).

The following examples will illustrate the practice of this invention; The examples provided are illustrative rather than exhaustive and do not in any way limit the claims of the patent.

EXAMPLE 1

Ornithine Methyl Ester Hydrochloride

In a clean dry 500 ml round bottom (RB) flask, methanol (187.5 ml) was taken and cooled to 10–15° C. Acetyl chloride (42 ml) was added dropwise at that temperature over 30 minutes. The mixture was stirred for 15 minutes (mts) and L-ornithine monohydrochloride (25 gm) was added slowly at 10–15° C. over 15 mts. After addition, the mass was stirred at its autogenous temperature for 15 mts and then was heated to reflux temperature slowly and maintained for 3 hrs. The reaction mass became a clear solution with progress of the reaction to completion.

After the completion of the reaction, methanol was distilled out (150 ml). The reaction mixture was cooled to 45–50° C. and 100 ml of acetone was added to the mass and stirred well for 1 hr at 15–20° C. for complete crystallization of the material. The material was filtered at room temperature (RT) and washed with small quantities of acetone. The product was sucked dry in a pump. It was dried for another 5 hrs in a vacuum oven at RT.

Yield: 31.5 g Melting Point: 192–194° C.

EXAMPLE 2

Methyl-2,5-di[1-(4-chlorophenyl) methylidene amino]pentanoate (Bis Schiff base)

Methylenedichloride (MDC) was taken in a clean, dry 1 L RB flask and under stirring and L-ornithine methyl ester dihydrochloride (60 gm) followed by p-chloro benzaldehyde (77 g) were charged as solids. The mixture was stirred well for 15 mts. The mass was cooled to 5–10° C. and Triethylamine (80 ml) was added slowly at 5–10° C. drop wise in a period of 3 hrs. After the addition was complete, the mass was stirred at RT for 15 hrs. As the reaction proceeded, Triethylamine hydrochloride precipitated out.

The reaction mass was filtered at RT and sucked dry thoroughly. The cake was washed with 100 ml of MDC and the filtrate was collected. Combined filtrates were washed with water twice (2×500 ml) and dried over sodium sulfate; MDC was distilled off completely. To the thick liquid, Hexane was added (500 ml) and stirred well to precipitate the product. Stirring was continued at RT for 2 hrs for complete precipitation and the product filtered. The product was suck-dried well and washed with hexane (100 ml). The product was dried under vacuum at RT.

Yield (dry): 92 gm Melting point: 95–97° C.

Analysis: $C_{20}H_{20}Cl_2N_2O_2$ Calculated: C, 61.39; H, 5.15; N, 7.16 Found: C, 61.16; H, 4.98; N, 7.26

EXAMPLE 3

Methyl-2,5-di[1-(3,4-chlorophenyl) methylidene amino]pentanoate (Bis Schiff base)

Use of 3,4-dichlobenzaldehyde in the place of 4-chlorobenzaldehyde in example 2 gave the title product.

Yield: 85% Melting point: 66–68° C.

Analysis: $C_{20}H_{18}Cl_4N_2O_2$ Calculated: C, 52.20; H, 3.94; N, 6.09 Found: C, 52.15; H, 3.88; N, 6.29

EXAMPLE 4

Methyl-2,5-di[1-(2,6-chlorophenyl) methylidene amino]pentanoate (Bis Schiff base)

Use of 2,6-dichlobenzaldehyde in the place of 4-chlorobenzaldehyde in example 2 gave the title product.

Yield: 83% Melting point: 95–97° C.

Analysis: $C_{20}H_{18}Cl_4N_2O_2$ Calculated: C, 52.20; H, 3.94; N, 6.09 Found: C, 52.13; H, 3.84; N, 5.99

EXAMPLE 5

Methyl-2,5-di[1-(3-nitrophenyl) methylidene amino]pentanoate

Use of 3-nitrobenzaldehyde in the place of 4-chlorobenzaldehyde, as described in example 2, gave the title product; The product was crystallized from methanol.

Yield: 80% Melting point: 103–105° C.

Analysis: $C_{20}H_{20}N_4O_6$ Calculated: C, 58.24; H, 4.89; N, 13.59 Found: C, 57.95; H, 4.89; N, 13.47

EXAMPLE 6

Methyl-2-[1-(4-chlorophenyl)methylideneamino-]-5-(1,3-dioxo-2,3-dihydro-1H-2 isoindolyl)pentanoate A suspension of $N^\delta$-phthaloyl ornithine methyl ester hydrochloride (10 g), p-chlorobenzaldehyde (4.5 g) in dichloromethane (100 ml) was cooled to ~10° C. and triethylamine (10 ml) was added dropwise during 5 minutes. The resulting clear solution was stirred at room temperature for a day. The reaction mixture was washed with 25 ml water, 10 ml brine and the organic layer was dried over sodium sulfate. Evaporation of solvent and addition of 40 ml hexane to the residue with stirring resulted in the formation of a white solid that was filtered, dried under vacuum for two hours.

Yield: 11.3 g Melting point: 117–119° C.

Analysis: $C_{21}H_{19}ClN_2O_4$ Calculated: C, 63.24; H, 4.80; N, 7.02 Found: C, 62.48; H, 4.72; N, 6.69

EXAMPLE 7

Methyl 2,3-di(2-nitrophenyl)perhydropyrrolo (1,2-a)imidazole-7a carboxylate

In a 250 ml round-bottomed flask equipped with a magnetic stirrer were taken a mixture of ornithine methyl ester dihydrochloride (5.0 g) and 2-nitrobenzaldehyde (7.5 g) in MDC (70 ml). The suspension was stirred at 0° C. for 15 mts. Triethylamine (4.64 g in 10 ml MDC) was added slowly. The reaction mixture was then allowed to stir at RT overnight. The reaction mixture was diluted with MDC, washed with water twice and dried over sodium sulfate. MDC was evaporated to give the crude product which was crystallized from methanol to give a white crystalline solid.

Yield: 5.6 g Melting point: 126–128° C.

Analysis: $C_{20}H_{20}N_4O_6$ Calculated: C, 58.24; H, 4.89; N, 13.59 Found: C, 58.00; H, 4.75; N, 13.54

EXAMPLE 8

α-Difluoromethyl Ornithine Hydrochloride Monohydrate

Solid methyl-2,5-di[1-(4-chlorophenyl) methylidene amino] pentanoate (90 g) was taken in a dry one liter round bottomed reaction flask and cooled to 10–15° C. Under an atmosphere of nitrogen, lithiumhexamethyldisilazide (360 ml, 1M solution in tetrahydrofuran ((THF))) was added over a period of 20 minutes. It was stirred and a clear solution was obtained. Stirring was continued for another 2 hrs. It was then cooled to 5–10° C. and difluorochloromethane gas was passed through the reaction mass until thin layer chromatography (TLC) indicated the completion of reaction. The reaction mass was kept under the static atmosphere of the difluorochloromethane gas for a few more hours. Then THF was removed carefully and the volume was brought to around 200 ml. To this mass, water (500 ml) was added and stirred well. The product was extracted thoroughly with MDC and the MDC layer was washed with water and MDC was removed. To the thick mass, 500 ml of 1N HCl was added and the reaction mass was stirred for 20 hrs at RT. Then the mass was extracted well with MDC and the aqueous layer was subjected to vacuum distillation. It resulted in the formation of Eflornithine methyl ester hydrochloride. This was hydrolyzed with ION HCl (400 ml) for about 6 hrs. The aqueous reaction mixture was distilled under vacuum and ethanol was added to precipitate the crude product under chilled conditions. The crude product was filtered and crystallized from water-ethanol to yield about a first crop of 18 g of Eflornithine hydrochloride monohydrate.

Analysis: $C_6H_{15}ClF_2N_2O_3$ Calculated: C, 30.45; H, 6.39; N, 11.84 Found: C, 30.39; H, 6.22; N, 11.65

EXAMPLE 9

α-Difluoromethyl Ornithine Hydrochloride Monohydrate (Eflornithine Hydrochloride Monohydrate)

The substrate was Methyl-2-[1-(4-chlorophenyl)methylideneamino]-5-(1,3-dioxo-2,3-dihydro-1H-2-isoindolyl) pentanoate and the alkylation procedure was the same as in Example 6. The product, Eflornithine hydrochloride monohydrate was isolated by acid hydrolysis as described in Example 8.

EXAMPLE 10

α-Difluoromethyl Ornithine Hydrochloride Monohydrate

Into a dry 100 ml three necked RB flask equipped with a stirrer, gas inlet and outlet arrangement methyl-2,5-di[1-(3, 4-chlorophenyl) methylidene amino] pentanoate (2.0 g) and sodium hydride (0.21 g) in dry THF (20 ml) were added. The resulting suspension was stirred at 50° C. under a nitrogen atmosphere for 2 hrs. The reaction mixture was then cooled to 5° C. and the nitrogen inlet was replaced with chlorodifluoromethane gas tube. The gas was passed for about 45 mts. The reaction was stirred at RT and allowed to stand overnight. The reaction mixture was worked up by quenching with water and the pH was adjusted to 2 with aqueous HCl. The reaction mixture was extracted with MDC twice. The water layer was concentrated and taken up in methanol and chilled. The crystallized inorganic material was removed. The filtrate was concentrated and the residue taken up in 6N HCl and hydrolyzed. The resulting aqueous layer was evaporated. The crude product was dissolved in ethanol, chilled again to remove any inorganic material and further purified by water-acetone to give a product with a melting point (mp) 223–225° C. with spectral data such as NMR matching with material obtained in Example 8.

What is claimed is:

1. A process to manufacture-Difluoromethylornithine, its analogs and derivatives represented by formula I

I wherein $R_1$ is hydrogen;

$R_2$ is hydroxy, $C_1$–$C_8$ alkoxy, —NR'R", wherein R' and R" are independently hydrogen, $C_1$–$C_8$ alkyl groups;

$R_3$ is hydrogen;

$R_4$ is —$CH_2F$, —$CHF_2$, —$CF_3$ and the salts thereof, and the process comprising the step of hydrolyzing the halomethylated compounds of formula IIA, under acid conditions;

IIa wherein:

$R_4$ is —$CH_2F$, —$CHF_2$, —$CF_3$, $R_5$ is hydrogen, $C_1$–$C_8$ alkyl groups;

$R_6$ is monohalogen substituents such as o,m,p-chloro or o,m,p-bromo; or dihalogen substituents such as 3,4-dichloro; 2,6-dichloro; 3,4-dibromo and other positional isomers thereof; or polyalkoxy substituents; and $R_7$ is $C_1$–$C_4$ alkyl, halogens such as chlorine or bromine.

* * * * *